United States Patent [19]
Björkman

[11] Patent Number: 4,909,992
[45] Date of Patent: Mar. 20, 1990

[54] DEVICE FOR HANDLING POROUS MATRIXES AND AN ANALYSIS APPARATUS COMPRISING THE SAME

[75] Inventor: Rune Björkman, Bälinge, Sweden
[73] Assignee: Pharmacia AB, Upsala, Sweden
[21] Appl. No.: 131,362
[22] Filed: Dec. 10, 1987

Related U.S. Application Data

[63] Continuation of Ser. No. 758,217, Jul. 1, 1985, abandoned.

[51] Int. Cl.⁴ .................... B01L 3/00; G01N 35/06
[52] U.S. Cl. .................... 422/100; 422/63; 422/69; 422/101; 422/104; 436/809; 435/805
[58] Field of Search ............ 435/805; 436/809, 810, 436/535; 15/119 A; 422/63–67, 69, 72, 73, 100, 99, 101, 71, 104

[56] References Cited

U.S. PATENT DOCUMENTS

| | | | |
|---|---|---|---|
| 2,789,307 | 4/1957 | Sussman | 15/119 A |
| 3,161,905 | 12/1964 | Dryden | 15/119 A |
| 3,560,162 | 2/1971 | Mittleman | 422/73 |
| 4,200,613 | 4/1980 | Alfrey et al. | 422/71 |
| 4,216,562 | 8/1980 | Strahs | 15/119 A |
| 4,438,540 | 3/1984 | Senour | 15/119 A |
| 4,483,925 | 11/1984 | Noack | 42/101 |

Primary Examiner—Michael S. Marcus
Attorney, Agent, or Firm—Fred Philpitt

[57] ABSTRACT

A device for handling porous solid matrixes (16) in analytic determinations of the type comprising at least one reaction step, which is performed in the very matrixes by absorption of a liquid phase therein, comprises a holder (1) and at least one matrix carrier (2), each of which can retain a matrix (16) while at the same time permitting liquid which surrounds the matrix carrier to substantially unobstructedly be absorbed by the matrix. The holder (1) is provided with at least one gripping body (11) projecting therefrom, each of which can detachably carry a corresponding matrix carrier (2), and at least one squeezing body (11), each of which can be pressed against the porous matrix for squeezing out liquid from the same.

An analysis apparatus comprises such a handling device, the holder (1) of which is carried by a driving mechanism in the apparatus, which driving mechanism has driving means for both horizontal and vertical displacement of the holder (1), so that matrix carriers (2) carried by the same can be moved horizontally between adjacent liquid containers (29, 29', 30) and vertically down into and up from selected liquid containers.

21 Claims, 5 Drawing Sheets

DEVICE FOR HANDLING POROUS MATRIXES AND AN ANALYSIS APPARATUS COMPRISING THE SAME

This is a continuation of application Ser. No. 758,217, filed July 1, 1985 abandoned and the benefits of 35 USC 120 are claimed relative to it.

TECHNICAL FIELD

The present invention relates to a device for handling porous matrixes and to an analysis apparatus for use in analytical determination methods, in particular such based on biospecific reactions in heterogeneous systems, e.g. biospecific affinity reactions between a receptor and a ligand. More specifically the invention is concerned with determination methods of this kind, wherein one or more reactions are carried out within a solid phase having the form of a porous body in which a liquid phase is absorbed.

BACKGROUND OF THE INVENTION

A great number of biochemical determination reactions are based on biospecific affinity reactions between a receptor and a ligand. As examples of such reactions can be mentioned immunochemical reactions between an antigen and an antibody, enzymatic determination methods such as enzyme-substrate or enzyme-coenzyme, lektin-sugar, etc. Usually the ligand is the component to be determined. It is dissolved in a liquid, whereas the receptor is immobilized on a carrier in contact with the liquid. By letting a known amount of the ligand, which is labelled with an indicatable group, a so-called marker, compete with the unlabelled ligand one can determine the amount of unlabelled ligand which is present in a sample. Alternatively the measurement can be performed by adding an excess of the labelled ligand after the reaction with the unlabelled ligand.

In for example Radio Immuno Assay, so-called RIA technique, radioactive isotopes are used as markers. In this technique e.g. antigen molecules are allowed to compete in a sample with added isotope-labelled antigen molecules for the available sites on antibodies which are bonded to the carrier. After the reaction non-bonded material is removed by washing, the amount of residual activity on the carrier being an indication of the antigen concentration in the sample. As mentioned above one can, as an alternative, add the antigen sample to the carrier before the addition of the isotope-labelled antigen. An alternative determination method is Enzyme Immuno Assay (so-called EIA technique), wherein chromogenic or fluorgenic markers are used instead of radioactive markers, but for the rest the EIA technique is analogous with the RIA technique.

In these and similar biospecific determination methods in heterogeneous systems various types of material of varying physical forms have been used as carriers or solid phase. Examples of carriers which have been used are small balls of gel-forming materials such as cross-linked polysaccharides, polyacrylamide and the like or of cellulose, small paper discs, the inner surface of test tubes, etc. It has also been suggested to use matrix bodies with open pores ("sponges") having such a pore size that they absorb the liquid phase and retain the same so that the reaction proceeds within the solid phase.

The porous matrixes have several advantages compared to other matrix materials, not the least in that the reaction speed can be optimized because of the large surface area for the reaction. A drawback of the prior art systems using porous matrixes—and of most other solid matrixes—has been the difficulties to handle the matrixes in a simple manner during the various steps of the analysis, especially the handling between reaction steps, washing steps and measurement.

In the published Swedish patent application No. 7305361-3 there is disclosed a porous matrix and its use for determining the contents of a special enzyme in a serum sample. The disclosed matrix is formed as an elastically compressible sponge of synfthetic material, e.g. polyurethane, and it is covered with a layer of hormone-binding proteins and antibodies such as insuline antibodies. The porous sponge is placed in a reaction tube which on top of the sponge has a manually actuable piston which seals against the tube wall and is designed to compress the sponge to make the same free from occluded air. The bottom of the reaction tube is provided with a comparatively small nozzle which can be closed. The reaction liquid is sucked into the sponge by compressing the same manually, while the bottom channel is open, by means of the piston The piston is then withdrawn, thereby causing sample solution and radioactive reaction solution to be sucked into the sponge. After the absorption of liquid the bottom nozzle is closed and incubation is performed for several hours, whereupon the absorbed liquid is squeezed out by means of the piston and the radioactivity of the sponge or of the expelled liquid is measured. As an alternative the sample may be absorbed and incubated first, the reaction solution being absorbed and incubated in a separate step after the sample solution has been expelled by means of the piston. This known analysis device is thus handled entirely manually by actuation of the piston, and the problems involved in intermediate washing steps are not at all mentioned. Furthermore, the suction procedure is complicated since it requires both manual compression of the piston and withdrawal of the same for creating the necessary suction force. In summary the device according to the published Swedish patent application No. 7305361-3 involves a complex procedure which is not suitable for automation, and the liquid-retaining properties of the matrix are not used at all.

SE-A-7507846-9 (423 457) discloses a system for washing ball-shaped bodies, which can be used for immunoassays. These balls are not porous and cannot be compressed.

OBJECT OF THE INVENTION

The present invention aims at improving and simplifying the handling of porous matrixes in analytical determination methods, wherein one or more reactions take place in the very matrix. A more specific object of the invention is to provide a novel type of handling device for the porous matrixes, so that they can be moved very easily between different treatment steps such as reaction, incubation, washing and measurement. A further object of the invention is to make possible automation (fully-automatic or semi-automatic) of this type of determination methods, using means which are simple, inexpensive and easy to manufacture. A further object of the invention is to make it possible, during the progress of the analysis, on the one hand to compress the porous matrix for expelling liquid, on the other hand to apply a suction pressure to the matrix for through-suction of e.g. washing liquid and/or for sucking the matrix dry. Further objects of the invention will appear from the following description of the invention and specialembodiments thereof.

SUMMARY OF THE INVENTION

One object of the invention is a device for handling porous solid matrixes in analytical determinations comprising at least one reaction step, which is performed in the very matrixes by absorption of a liquid phase therein. The device according to the invention comprises a holder and at least one matrix carrier. Each matrix carrier is capable of retaining a matrix while at the same time permitting liquid surrounding the matrix carrier to substantially unobstructedly be absorbed by the matrix. The holder is provided with at least one gripping body projecting therefrom, each gripping body being capable of detachably carrying a matrix carrier, and at least one squeezing body, each of which can be pressed against the porous matrix for expelling liquid from the same.

Another object of the invention is an analysis apparatus for automatic or semi-automatic handling of porous solid matrixes in analytical determinations of the type comprising at least one reaction step which is performed in the very matrixes by absorption of a liquid phase therein. The analysis apparatus in accordance with the invention comprises a handling device according to the above, whose holder is carried by a driving mechanism in the apparatus. This driving mechanism has driving means for both horizontal and vertical displacement of the holder so that matrix carriers carried by the holder can be moved horizontally between adjacent liquid containers and vertically for insertion into and withdrawal from selected liquid containers.

Preferred embodiments of the handling device and the analysis apparatus according to the invention are indicated in the subclaims.

The invention can advantageously be applied in immuno assay techniques, e.g. RIA and EIA (using chromogenic as well as fluorgenic substrates), but it can also in principle be used in any method of analysis utilizing a porous matrix, which can absorb a liquid phase for reaction in the matrix. The porous matrix, which forms a "self-contained" reaction vessel, can e.g. consist of porous cellulose, a porous synthetic polymer such as porous polyurethane, etc. The matrix should, of course, be capable of absorbing a liquid phase in the indicated manner, and it is preferably elastically compressible at least in its wet condition.

DESCRIPTION OF PREFERRED EMBODIMENTS

A few examples of preferred embodiments of the invention will now be described with reference to the enclosed drawings. It should, however, be emphasized that this description is not intended to limit the scope of the invention, but it is merely intended to give illustrative examples of how the invention may be put into practice. The invention can thus be modified and varied in many ways within the scope of the enclosed claims.

Figure 1:
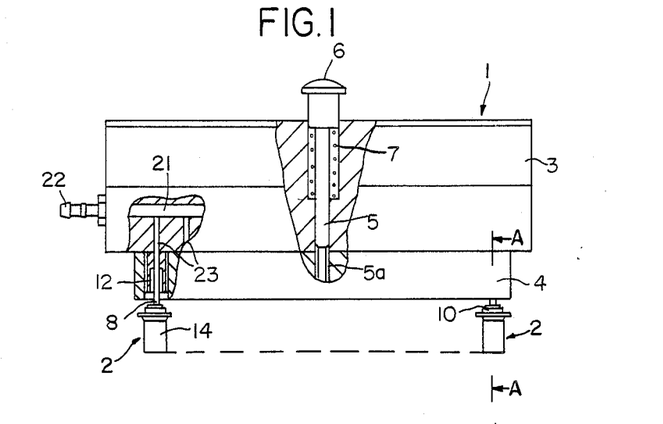
FIGS. 1 and 2 are elevation views, partly in section, showing a preferred embodiment of a matrix handling device according to the invention with and without matrix carriers carried thereby.
Figure 2:
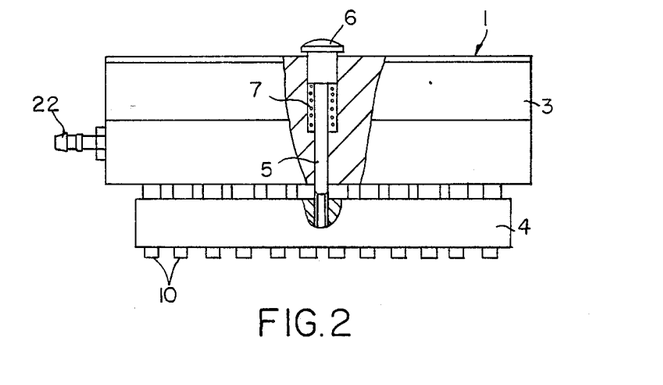
Figure 3:
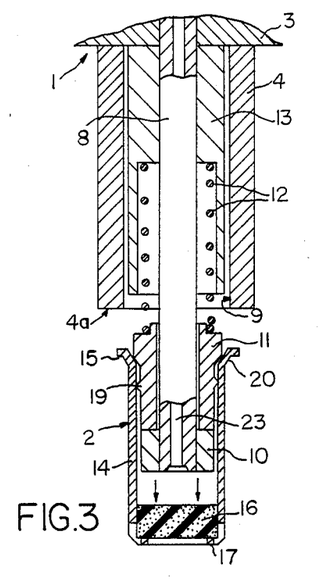
FIG. 3 is a part sectional view of the matrix handling device according to FIGS. 1 and 2, taken substantially along A—A in FIG. 1.

The matrix handling device shown in FIGS. 1–3 basically consists of a holder 1 and a plurality matrix carriers 2. In the shown embodiment the holder 1 has a stationary part 3 and a part 4 which is movable in relation to the stationary part. The movable holder part 4 is carried by the stationary holder part 3 by means of a central shaft 5, which is slidingly journalled in the part 3 and the bottom end 5a which is secured to the movable holder part 4. The opposite end of the shaft 5 is provided with an actuation knob 6 which is acted upon by a compression spring 7 located in a recess provided in the stationary holder part 3. The spring 7 biases the movable holder part 4 towards the stationary holder part 3, so that the holder normally takes the position shown in FIG. 1.

The stationary holder part 3 is further provided with a plurality of tubes 8—one for each matrix—which project from the bottom side of the holder part 3, pass through recesses 9 provided in the movable holder part 4 and project from the bottom side of the same. As best can be seen in FIG. 3 a squeezing body 10, e.g. made of plastics material, is attached to the bottom end of each tube 8. A gripping body 11 is slidingly carried by each tube 8, inwardly of the squeezing body 10. Each gripping body 11 is kept biased against the corresponding squeezing body 10 by means of a compression spring 12 acting between the gripping body 11 and a guiding body 13 located in the corresponding recess 9 of the movable holder part.

Figure 4A:
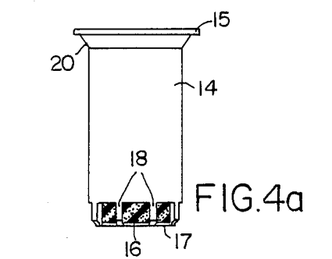
FIGS. 4A and 4B show the matrix carrier according to FIG. 3 in elevational view and bottom view respectively.
Figure 4B:
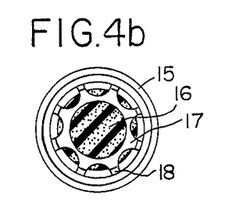
Figure 5A:
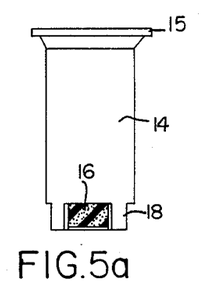
FIGS. 5A and 5B show a second embodiment of the matrix carrier in elevational view and bottom view respectively.
Figure 5B:
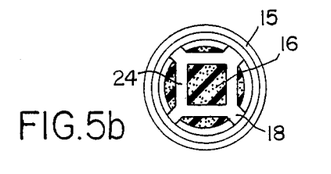

In the embodiment shown in FIGS. 3, 4A, 4B the matrix carrier 2 is designed as a tube 14 which at the top is provided with a collar 15 and which at least at its bottom portion has a large open area, so that liquid can be absorbed substantially unobstructedly by the porous matrix 16. In the embodiment according to FIGS. 3, 4A, 4B the matrix 16 is retained in the tube 14 by means of a thin ring 17 having an opening of smaller diameter than the inner diameter of the tube 14 (and the outer diameter of the matrix 16). The supporting rint 17 is attached to the tube 14 by means of thin attachments legs 18. The tube 14, the support ring 17 and the attachment legs 18 are preferably made of a single piece of material such as a suitable plastics material.

The gripping body 11 can be detachably inserted into the tube 14. The gripping effect can be provided in any suitable manner, but some kind of friction engagement between the gripping body 11 and the tube 14 is usually preferred. This can e.g. be achieved by making the gripping body 11 slightly tapered towards its outer end, if desired using projections 19 for increasing the friction. The gripping body 11, which preferably is made of a suitable plastics material, is preferably also at the top provided with an enlarged abutment portion 20 or any other stop means preventing the gripping body from being inserted too far into the tube 14.

The matrix handling device shown in FIGS. 1-3 can be used in the following way. The desired number of matrix carriers 2 are applied to the corresponding gripping bodies 11 by pressing the same into the tubes 14. This can e.g. be done by placing the tubes 14 in holes or wells having the same center distance as the center distance between the gripping bodies 11 such as the wells of commercially available so-called microtiter strips. The tube collars 15 keep the tubes at the same level in the wells. The holder 1 is moved towards the prepared matrix carriers while pressing the gripping bodies 11 into the corresponding carrier tubes 14 (and under compression of the springs 12). The handling device now takes the position shown in FIG. 1, in which it carries a series of matrix carriers 2 which in a very simple manner can be conveyed simultaneously between different treatment stations and be subjected to various reaction and treatment steps during the analysis. For example, all matrix carriers can be immersed simultaneously into a corresponding number of wells of a microtiter strip containing a suitable sample solution. Thanks to the large open area at the bottom of the carrier tubes 14 the sample solution is absorbed by the porous matrix 16. According to the requirements in the analysis to be performed the matrix carriers 2 can be left in the sample solution wells together with the holder 1 or they may be loosened from the holder and left in the wells for e.g. incubation. In the latter case the holder 1 can during the incubation period be used for handling a new set of matrix carriers. The matrixes 16 of the matrix carriers 2 can also in a simple manner of compressed for expelling the liquid adsorbed in the matrixes. The utility of the handling device in various specific applications will be described further in connection with FIGS. 7-9 below.

If one wishes to remove the matrix carriers 2 from the gripping bodies 11 of the holder, this can be done in a very simple manner by pressing the actuating knob 6, whereby the movable holder part 4 is pushed away from the stationary holder part 3. In doing so the bottom edges 4a of the movable holder part 4 contact the tube collars 15. Since the gripping bodies 11 at the same time retain their distance from the stationary part 3 of the holder, the movable part 4 will eject the carrier tubes 14 from the gripping bodies 11. Although it is very advantageous to provide the holder 1 with such an ejection mechanism for the matrix carriers, it is to be emphasized that the device according to the invention offers advantages as to handling also without having this function. The invention is thus also intended to comprise holders 1 not having any particular mechanism for ejection of the tubes (i.e. the movable holder part 4). In this case one can use a separate device for loosening the matrix carriers, e.g. corresponding to the detail 34 in FIG. 7.

The described step of squeezing out or expelling the liquid which has been absorbed in the matrixes 16 is performed by pressing the holder with the attached matrix carriers against a support surface such as a filter paper, the bottom of a holder for rinsing liquid, etc. On pressing against the support the squeezing bodies 10 will compress the matrixes 16 (as indicated by the arrows in FIG. 3). It is to be underlined that the same results is achieved when the tube collars 15 (instead of the bottom of the tubes) are applied against a stationary abutment such as the possibly elevated top edges of the wells of microtiter strip. In this manner liquid can be squeezed out from the matrixes without the bottoms of the tubes 14 contacting the support.

In the embodiment shown in FIG. 1 the holder 1 is provided with a further function, viz. means for sucking the matrixes 16 dry. To this end the stationary holder part 3 is provided with a common suction channel or manifold 21, which can be connected to a suitable suction device, e.g. a suction pump or jet water suction, via a connection nipple 22. A plurality of branch channels 23, opening at the respective squeezing body 10, are connected to the common channel 21. The channels 23 are preferably formed by the inner cavities of the tubes 8 carrying the squeezing bodies 10. The suction system 21-23 is used e.g. when one wishes to flush rinsing liquid through the matrixes 16 or suck the same dry, and it can be combined with repeated squeezing of the matrixes 16 in the above indicated manner.

Figure 6A:
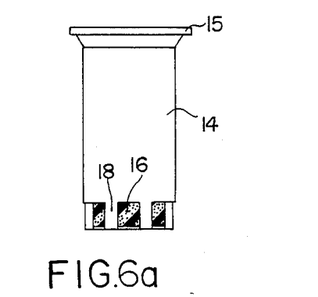
FIGS. 6A and 6B show a third embodiment of the matrix carrier in elevational view and bottom view respectively.
Figure 6B:
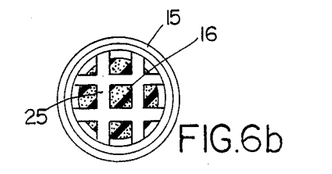

FIGS. 5A, 5B and 6A, 6B show examples of some alternative embodiments of the tube 14 carrying the matrix 16, the corresponding elements having the same reference designations as in FIGS. 4A, 4B. In the embodiment shown in FIGS. 5A, 5B the annular bottom portion 17 of FIGS. 4A, 4B has been replaced by a square bottom portion 24, whereas FIGS. 6A, 6B show a check-pattern bottom portion 25. The shown alternative embodiments of the matrix carrier are all primarily intended to be made as unitary parts of plastics materials, but it is within the scope of the invention possible to use matrix carriers of other materials and having other shapes. The requirements on the matrix carrier is primarily that it should be capable of physically retaining the matrix carrier 16 and at the same time provide substantially unobstructed access of liquid to the same, and it should be capable of being detachably held by the gripping bodies 11. Of course, the openings provided in the matrix carriers need not be restricted to the bottom portions thereof.

Figure 7:
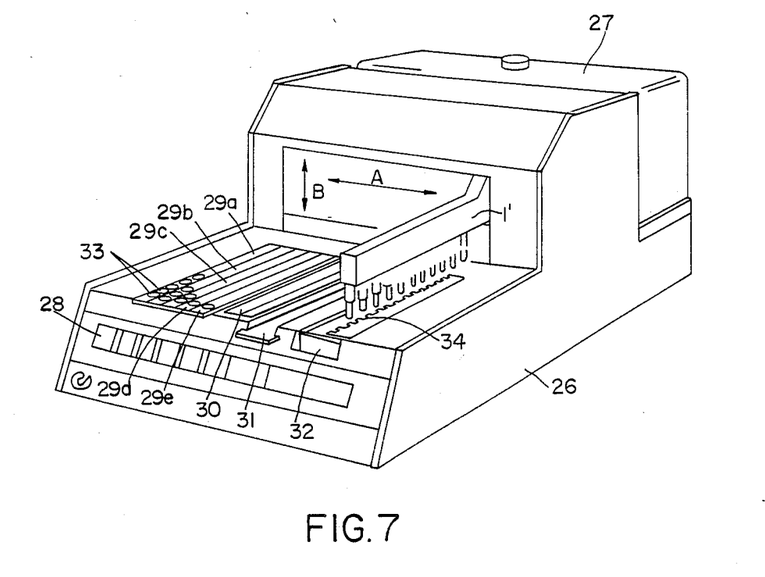
FIG. 7 is a perspective view of a first embodiment of an automated analysis device according to the invention.

FIG. 7 shows a first embodiment of an automated analysis device according to the invention, which is provided with a matrix carrier holder 1' substantially corresponding to the one according to FIGS. 1 to 3 but without the movable holder part 4 serving the function of an ejection device. The analysis apparatus shown in FIG. 7 comprises a stationary frame 26 having a container 27 for rinsing liquid. In the apparatus frame 26 there are provided driving devices (not shown) which carry one end of the matrix carrier holder 1' and can move the same horizontally, as indicated by the arrow A, and vertically, as indicated by the arrow B. The analysis apparatus is further provided with a control panel 28 and suitable recesses, in which microtiter strips 29a-e, a washing container 30, a filter strip 31 and a collection container 32 for used matrix carriers can be placed. Each microtiter strip 29a-e comprises a plurality of wells 33, e.g. twelve. The analysis apparatus is further provided with a program and electronic unit (not shown) which i.a. comprises printed circuit cards containing suitable functional programs for different types of analyses, control electronics, driving circuits for the motors for the holder arm 1', etc. The specific design of the program and electronic unit, the driving motors for the matrix carrier holder 1', pumping means, etc. is not critical for the invention, but a person of ordinary skill in the art can easily select suitable constructional elements by means of the functional description given herein.

Figure 9:
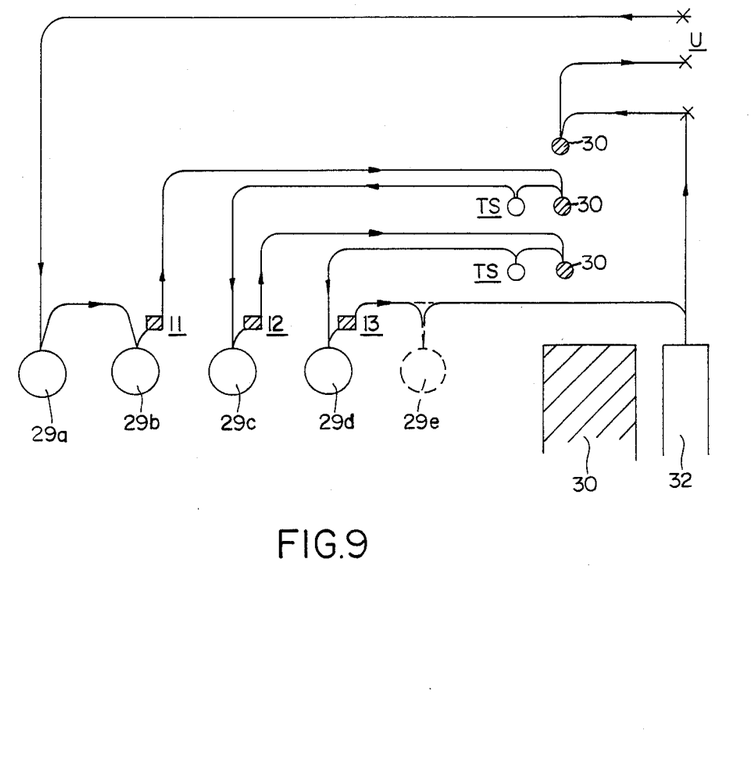
FIG. 9 is flow chart illustrating the method of operation of the analysis devices according to FIGS. 7 and 8.

The analysis apparatus shown in FIG. 7 can e.g. be used in the following EIA-test, reference also being made to the functional diagram of FIG. 9.

As a preparation for the analysis the matrix carriers 2 are placed in the wells 33 of the first microtiter strip 29a. The sample solutions to be analized are pipetted into the wells of the micro strip 29b, e.g. with 50 μl of sample solution in each well. Conjugate solution, substrate solution and stop solution are dispensed into the wells of the micro strips 29c, 29d and 29e respectively. The container 30 for washing liquid is filled with washing liquid from the container 27 and a filter strip 31 is put into its holder. The desired program is set on the control panel 28, whereupon the analysis is carried out automatically as follows.

Collection of matrix carriers.

The holder 1' is moved from the starting position (U) horizontally to a position above the microtiter strip 29a, in which position it is lowered to grip the matrix carriers (compare FIG. 1).

Incubation 1.

The holder 1', together with the matrix carriers 2 carried thereby, is raised and then moved to a position above the microtiter strip 29b, in which position it is lowered into the wells containing sample solution, so that the porous matrix 16 can absorbe sample solution. The holder is then kept in a waiting position during the desired incubation time (I1 in FIG. 9).

Washing step 1.

The holder 1' is in a corresponding manner moved to a position above the container 30 containing washing liquid and the suction pump is started for sucking the matrixes dry (TS). At the same time the matrix carriers are lowered into the washing container 30 with continued suction. In order to increase the washing effect the matrixes are squeezed a couple of times by means of the squeezing bodies 10 as has been described with reference to FIG. 3. The holder 1' is moved upwards and the matrixes are sucked dry. When necessary the washing step is repeated one or more times. The suction pump is switched off.

Incubation 2.

The holder 1' is moved to a position above the microtiter strip 29c, is lowered so that the matrixes absorb the conjugate solution and is kept in a waiting position until the set incubation period has lapsed (I2).

Washing step 2.

Is carried out fully in analogy with Washing step 1, if desired using a different number of washings.

Incubation 3.

Is carried out in analogy with Incubation steps 1 and 2 but with absorption of substrate solution in the microtiter strip 29d.

Stop solution.

In analogous manner the holder 1' is moved to a position above the microtiter strip 29e, the matrixes are lowered into the stop solution for a few seconds, then the holder 1' is again raised.

Reading.

The holder 1' is moved to a position above the filter strip 31, lowered towards the same and the reaction solutions absorbed in the matrixes are transferred to the filter strip by squeezing by means of the squeezing bodies 11. The filter strip 31 is removed (manually) and the colour intensity of the deposited spots are compared with a standard.

Removal of matrix carriers.

The holder 1' is moved to a position above the collection container 32 and is lowered so that the tube collars 15 of the matrix carriers will be located under the recesses 34 of a wipe-off edge. On repeated raising of the holder 1' the matrix carriers 2 are retained by the wipe-off edge and are thereby removed from the gripping bodies 11 so that they fall into the container 32 (compare FIG. 2).

Rinsing of the apparatus.

The holder 1' (without matrix carriers) is moved to the washing pool 30 and sucks the desired amount of washing solution through. The holder 1' then returns to the starting position according to FIG. 7, after which the apparatus is ready for re-use.

If desired the analysis apparatus can be provided with acoustic and/or optical devices indicating that the analysis has been completed. The used matrix carriers and microtiter strips can be removed from the apparatus and discarded.

Figure 8:
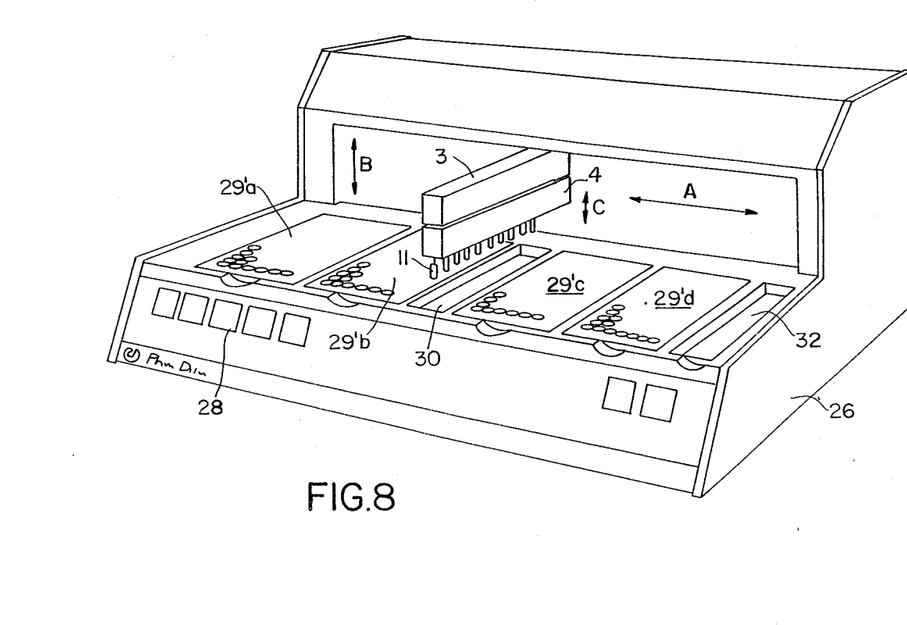
FIG. 8 is a schematic perspective view of a second embodiment of an automated analysis device according to the invention.

The alternative embodiment of the analysis apparatus according to the invention which is shown in FIG. 8 differs from the embodiment according to FIG. 7 primarily in that so-called microtiter plates 29'a–d are used instead of the microtiter strips 29a–e of FIG. 7, and in that the matrix carrier 1 is provided with a built-in mechanism for ejection of the matrix carriers, like in the embodiment according to FIGS. 1–3. As is well known to a person skilled in the art a microtiter plate comprises a plurality of rows of adjacent wells, such as eight rows each containing twelve wells. In the embodiment according to FIG. 8 the manual actuation knob 6 (see FIGS. 1 and 2) is preferably replaced by a suitable device, which is built-in in the driving system for the movements of the holder 1 and which moves the movable holder part 4 downwards from the stationary holder part 3 when the matrix carriers are to be removed from the holder. This is marked by the arrow C in FIG. 8. Also this movement is controlled by the program unit of the apparatus.

The analysis apparatus shown in FIG. 8 can e.g. be used as follows for performing a RIA-test. Matrix carriers are placed in the wells of the microtiter plate 29'a. The desired amount of sample solution, e.g. 50 μl, is dispensed in the wells of the microtiter plate 29'b and the desired amount of tracer solution, e.g. 50 μl, in the wells of the microtiter plate 29'c. The desired test procedure is set on the control panel 28 and the analysis is started. The holder 1 first moves to and collects the first row of micro carriers in the microtiter plate 29'a and transports the same to the first row of sample solution wells in the microtiter plate 29'b. After the matrix carriers have been placed in the sample solution wells they are loosened from the gripping bodies 11 by moving the movable holder part 4 away from the stationary holder part 3. The holder 1 is then moved to the second row of wells in the microtiter plate 29'a for collecting another set of matrix carriers 2, which are then transported to the second row of sample solution wells 29'b for incubation. The holder 1 continues its motion between the microtiter plates 29'a and 29'b until all of the matrix carriers have been positioned in the corresponding sample solution wells for incubation. When the incubation has been terminated the holder 1 collects the matrix carriers of the first row of the sample solution wells, performs the desired washing and dry-sucking in the same manner as has been described in connection with FIG. 7, and positions the washed matrix carriers in the first row of wells in the microtiter plate 29'c containing tracer solution. The matrix carriers are left in these wells by moving the movable holder part 4 downwards, the holder returns to the second row of matrix carriers in the microtiter plate 29'b, and so on until all of the matrix carriers have been washed and positioned in the tracer solution wells 29'c for incubation. When the incubation has been terminated the holder 1 collects the matrix carriers of the first row of the microtiter plate 29'c, washes and sucks dry and leaves the sucked-dry matrix carriers in the first row of wells in the microtiter plate 29'd. This procedure is repeated until all of the matrix carriers have been placed in the respective wells of the plate 29'd. The apparatus is then washed and returned to the starting position in the same manner as has been described in connection with FIG. 7. As an alternative the matrix carriers can be returned to the starting plate 29'a, which is now empty. The ready-treated matrixes, which have been placed in the microtiter plate 29'd (or 29'a or a special measuring container) are taken for measurement in a suitable gamma counter.

EXAMPLE 1

The following EIA-test for Chlamydia Trachomatis was carried out using the apparatus according to the invention. The procedure was as has been described in connection with FIG. 7. The used matrixes were round cushions of porous cellulose (Wettex ®, from Celloplast AB, Norrköping, Sweden) coupled with rabbit-antiserum against Chlamydia Trachomatis. 50 µl extracts containing 0, 56, 167 and 500 ng/ml respectively of the corresponding antigen were used as samples. 50 µl of rabbit-anti-Chlamydia-coupled β-galactosidase was used as the conjugate, and 75 µl of o-nitrophenyl-β-galactoside solution was used as the substrate. The stop solution consisted of 200 µl of 0.4M $Na_2CO_3$, and the washing solution was PBS containing 0.5% Tween ® 20. The ready-treated reaction solution was squeezed out from the matrixes and the absorption at 405 nm was measured in a photometer.

The incubation times were 30 minutes in the sample solution (I1), 30 minutes in the conjugate solution (I2) and 2 hours in the substrate solution (I3). During each of the washing steps the matrixes were suction-washed and compressed for 3×1 seconds. The following test results were recorded.

| Antigen concentration (ng/ml) | Absorption (405 nm) |
| --- | --- |
| 0 | 0.051 |
| 56 | 0.064 |
| 167 | 0.076 |
| 500 | 0.121 |

EXAMPLE 2

A RIA-test (RAST) was carried out using a Wettex ®-cushion coupled with Allergen t3 (birch pollen, from Pharmacia Diagnostics AB, Uppsala, Sweden). 50 µl reference sera containing 17.5, 3.5, 0.7 and 0.35 PRU/ml respectively were used as sample solutions. 50 µl of the corresponding tracer solution (anti-IgE-$^{125}$I) were used in each well, and 0.9% NaCl solution containing 0.5% Tween ® 20 was used as the washing solution. The incubation times were 1 hour in the sample solution and 3 hours in the tracer solution. The washing steps were performed during 3×2 seconds with suction washing and squeezing of the matrixes. After the second washing step the sucked-dry matrixes were transferred to a gamma counter for measuring the residual radioactivity.

The invention also offers further advantages in the tests which have been specifically described above. For example, matrix carriers with ready-to-use matrixes can be put in e.g. microtiter plates or microtiter strips already when packing the test kit. Matrix carriers for different tests can be arranged in a predetermined pattern so that they form panels or other combinations, or all matrix carriers in a whole plate can be intended for one and the same test. In use such strips, plates, etc., which have been prepared already in connection with the packing, can be placed directly in e.g. an analysis apparatus according to FIG. 7 or 8 (compare the microtiter strips 29a in FIG. 7 and the microtiter plate 29'a in FIG. 8).

If the precision requirements are not too great it can be sufficient to dip the matrixes into containers containing an excess of reagents. Thanks to the inherent "self dosing" properties of the porous matrix (i.e. the property of absorbing a relatively constant amount of liquid for a given material and a given size of the matrix) only a predetermined amount of the agent will be absorbed. The matrix is then withdrawn from the reagent solution for incubation in a suitable position. In such a case it is not necessary to provide separate reagent wells for each matrix, but one can use a common reagent container into which a plurality of matrixes are immersed.

Although the invention has been specifically described in connection with automated analysis apparatuses (FIGS. 7 and 8) it is to be emphasized that substantial advantages as to handling of the matrixes are achieved also in connection with analyses which are performed manually in a small scale, e.g. in a smaller surgery. In such a case the handling device is moved manually between the different sample, reagent and washing wells, etc. in corresponding manner. When no suction system is available the washing can be performed batch-wise, in which case the matrix carriers, after having been dipped into a washing liquid, can be pressed against an absorbing material so as to compress the matrixes and expel the liquid contained therein. This procedure is repeated a suitable number of times.

I claim:

1. A device for handling a plurality of porous solid matrixes (16) in analytical determinations of the type involving at least one reaction step that is carried out in said matrixes by the absorption of a liquid phase therein, which device comprises in combination
   (A) a plurality of matrix carriers (2) positioned at spaced apart intervals in a desired array, each matrix carrier (2) containing a porous, solid compressible matrix (16) which will permit liquid which comes in contact with the matrix carrier to be absorbed by said matrix in a substantially unobstructed manner, and
   (B) a holder (1) engageable with said plurality of matrix carriers (a), said holder being movable with respect to said matrix carriers
      (a) a plurality of elements (8) depending downwardly from said holder (1), said elements being disposed in an array that is compatable with said array of matrix carriers, (b) a gripping body (11) operatively associated with each of said downardly depending elements (8), each gripping body (11) being movable with respect to its associated matrix carriers (2) and being arranged to detachably engage a matrix carrier (2), and (c) a squeezing body (10) associated with each of said downwardly depending elements (8) which is adapted to be pressed against a porous solid compressible matrix (16) for squeezing liquids out from the porous solid matrix (16).

2. A device for handling porous solid matrixes (16) in analytical determinations of the type involving at least one reaction step that is carried out in the matrixes by absorption of a liquid phase therein, which device comprises a holder (1) and at least one matrix carrier (2)

each matrix carrier containing a porous, solid compressible matrix (16) while permitting liquid which comes in contact with the matrix carrier to be absorbed in a substantially unobstructed manner by the matrix, said holder (1) and matrix carrier (2) being movable relative to each other, said holder (1) being provided with (a) at least one gripping body (11) that is movable with respect to its associated matrix carrier (2) that is arranged to detachably engage the matrix carrier (2) and (b) at least one squeezing body (10) which is adapted to be pressed against the porous solid compressible matrix (16) for squeezing out liquid from the same.

3. A device according to claim 2 wherein the matrix carriers (2) are detachably carried by the gripping bodies (11) by frictional engagement with the same.

4. A device according to claim 2 which includes a device (4) for ejection of the matrix carriers (2) from the gripping bodies (11).

5. A device according to claim 2 wherein each squeezing body (10) is connected to a suction conduit (21-23) provided in the holder (1).

6. A device according to claim 5 wherein the suction conduit comprises a manifold (21) provided in the holder (1) and a plurality of branch channels (23) corresponding to the number of squeezing bodies (10), said branch channels (23) connecting the manifold (21) with the respective squeezing bodies (10) and preferably being formed by inner cavitities provided in the shafts (8) which carry the squeezing bodies (10).

7. An analysis apparatus for handling porous solid matrixes in analytical determinations of the type comprising at least one reaction step, which is carried out in the very matrixes by absorption of a liquid phase therein, which apparatus comprises a handling device according to claim 2, the holder (1) of which is carried by a driving mechanism in the apparatus, which driving mechanism has driving means for both horizontal and vertical displacement of the holder (1) so that the matrix carriers (2) which are carried by the same can be moved horizontally between different liquid containers (29, 29', 30) and vertically down into and up from selected liquid containers.

8. An analysis apparatus according to claim 7 which includes a program unit for controlling the horizontal and vertical movements of the holder (1) according to a preselected path of movement.

9. A device according to claim 2 wherein each squeezing body (10) is attached to the end of a shaft (8) depending downwardly from the holder (1), the corresponding gripping body (11) being carried by said shaft so that it can slide between the squeezing body (10) and the holder (1).

10. A device according to claim 9 wherein the matrix carriers (2) are detachably carried by the gripping bodies (11) by frictional engagement with the same.

11. A device according to claim 9 wherein each squeezing body (1) is connected to a suction conduit (21-23) provided in the holder (1).

12. A device according to claim 9 wherein the gripping bodies (11) are spring biased against the squeezing bodies (10).

13. A device according to claim 12 which includes a device (4) for ejection of the matrix carriers 82) from the gripping bodies (11).

14. A device according to claim 12 wherein the matrix carriers (2) are detachably carried by the gripping bodies (11) by frictional engagement with the same.

15. A device according to claim 12 wherein each squeezing body (1) is connected to a suction conduit (21-23) provided in the holder (1).

16. A device according to claim 2 which includes a device (4) for ejection of the matrix carriers (2) from the gripping bodies (11).

17. A device according to claim 16 wherein the matrix carriers (2) are detachably carried by the gripping bodies (11) by frictinal engagement with the same.

18. A device according to claim 16 wherein each squeezing body (10) is connected to a suction conduit (21-23) provided in the holder (1).

19. A device according to claim 16 wherein the holder (1) comprises a stationary part (3) and a movable part (4) which can be moved relative to the stationary part so as to contact the matrix carriers (2) for ejecting the same from the gripping bodies (11).

20. A device according to claim 19 wherein the matrix carriers (2) are detachably carried by the gripping bodies (11) by frictional engagement with the same.

21. A device according to claim 19 wherein each squeezing body (10) is connected to a suction conduit (21-23) provided in the holder (1).

* * * * *